US00PP23950P3

(12) United States Plant Patent
Williams

(10) Patent No.: US PP23,950 P3
(45) Date of Patent: Oct. 1, 2013

(54) ***LOMANDRA FLUVIATILIS* PLANT NAMED 'AU807'**

(50) Latin Name: *Lomandra fluviatilis*
Varietal Denomination: AU807

(76) Inventor: Jon Williams, Dural (AU)

( * ) Notice: Subject to any disclaimer, the term of this patent is extended or adjusted under 35 U.S.C. 154(b) by 82 days.

(21) Appl. No.: 13/374,283

(22) Filed: Dec. 21, 2011

(65) Prior Publication Data

US 2013/0167279 P1 Jun. 27, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

'AU807' is a distinctive variety of *Lomandra fluviatilis* which is characterized by a combination of improved vigor, short plant height, long and arching foliage and a high number of inflorescences borne on long peduncles.

3 Drawing Sheets

Latin name of the genus and species: The Latin name of the genus and species of the novel variety disclosed herein is *Lomandra fluviatilis.*

Variety denomination: The inventive variety of *Lomandra fluviatilis* disclosed herein has been given the variety denomination 'AU807'.

BACKGROUND OF THE INVENTION

The present invention relates to a new and distinct perennial herbaceous variety of *Lomandra fluviatilis*, which has been given the variety denomination of 'AU807'. Its market class is that of an ornamental grass-like plant. 'AU807' is intended for use in landscaping and as a decorative plant.

Parentage: The *Lomandra fluviatilis* variety 'AU807' was finally selected in 2007 in an Australian nursery in the state of New South Wales following a selection process carried out from 2004 to 2007 involving approximately 500 open pollinated seedlings of common-form *Lomandra fluviatilis* (unnamed) production stock. Several candidate plants were isolated in 2005 for further evaluation of mature plant height, density, bloom habit and vigor. 'AU807' was ultimately selected in August of 2007 for the combination of improved vigor in the way of faster growth rate compared to the parent plant, approximately 20% shorter plant height compared to the parent and other progeny, arching foliage as opposed to the semi-erect habit of the parent and other progeny and a high number of inflorescences borne on long peduncles.

Asexual Reproduction: 'AU807' was first propagated asexually by division at a wholesale nursery in Richmond, New South Wales, Australia in 2008 and has since been asexually propagated by division through several successive generations. The distinctive characteristics of the inventive 'AU807' variety are stable from generation to generation; clones of the variety produced by asexual reproduction maintain the distinguishing characteristics of the original plant.

SUMMARY OF THE INVENTION

'AU807' is a distinctive variety of *Lomandra fluviatilis* which is characterized by a combination of improved vigor, short plant height, long and arching foliage and a high number of inflorescences borne on long peduncles.

BOTANICAL DESCRIPTION OF THE PLANT

Figure 1:
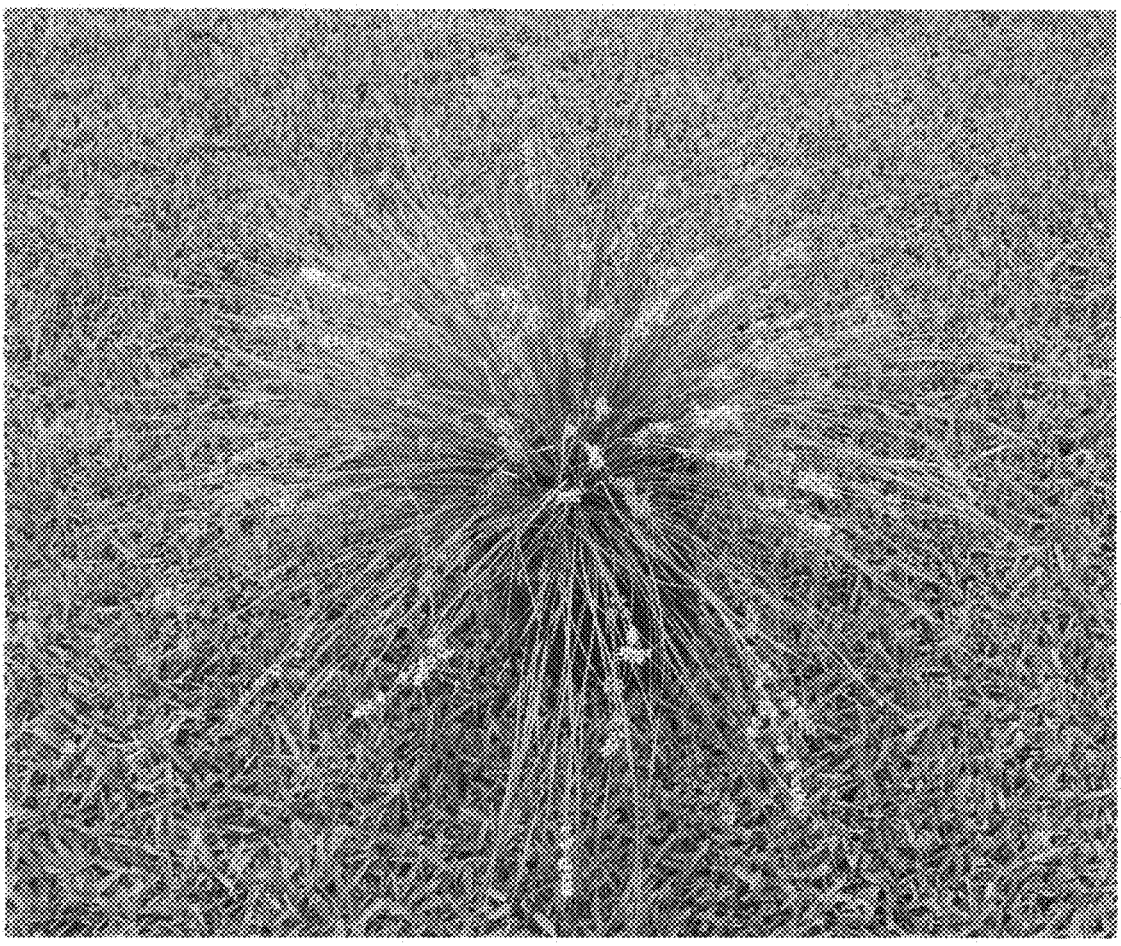
FIG. 1 shows a 10 month-old_sample 'AU807' plant from which Botanical Description data were collected.
Figure 2:
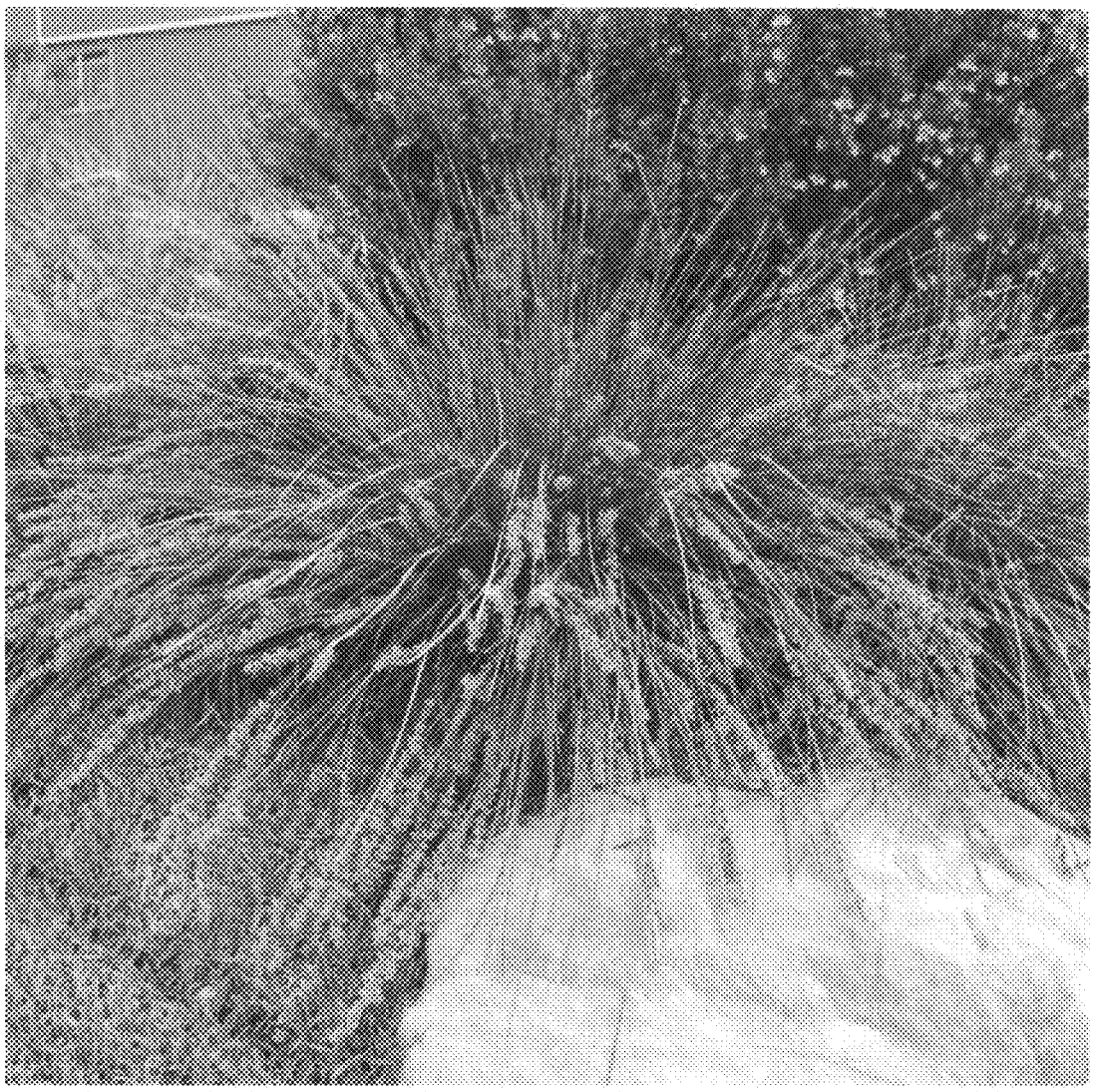
FIG. 2 shows a mature 'AU807' plant in the ground. Note the arching habit and the aspect of the racemes above the foliage.
Figure 3:
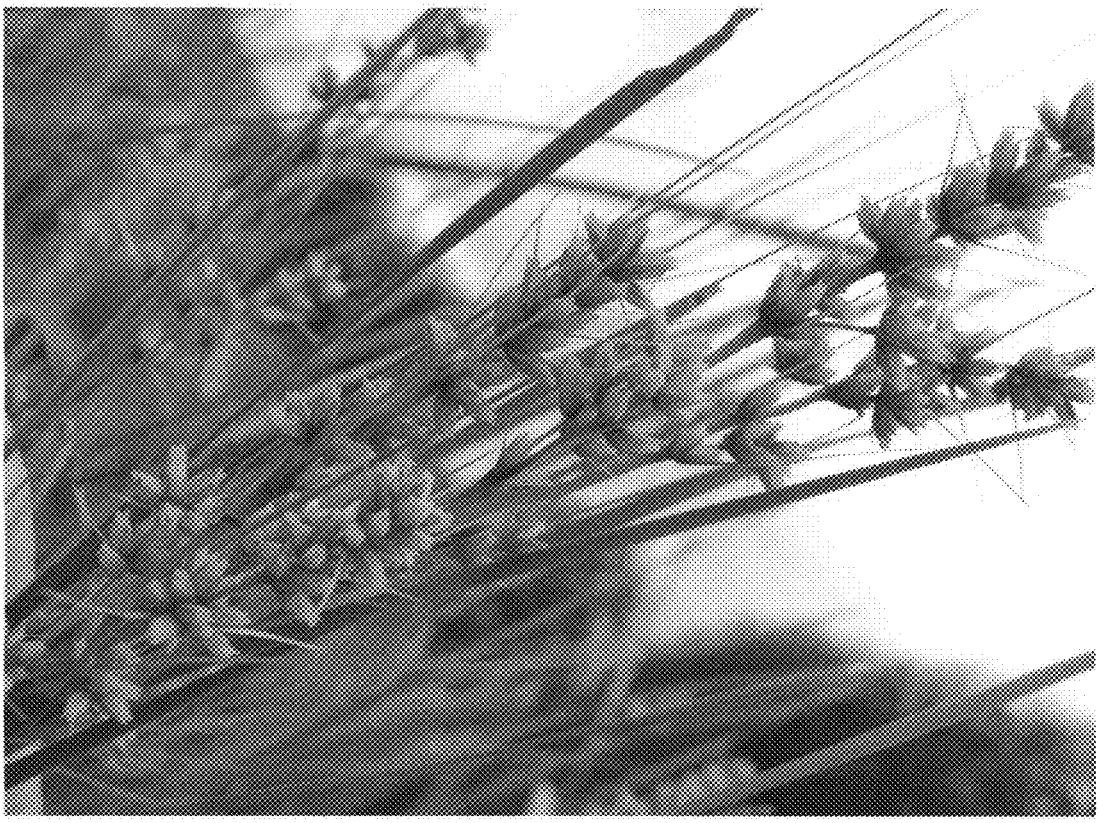
FIG. 3 shows a close up of the 'AU807' inflorescence.

The following is a detailed botanical description of a new and distinct variety of a *Lomandra fluviatilis* ornamental plant known as 'AU807'. Plant observations were made on 10 month-old plants grown in New South Wales, Australia. Unless indicated otherwise, the descriptions disclosed herein are based upon observations made from mature 'AU807' plants grown from rooted cuttings from November 2010 to September 2011 in 200 mm nursery pots. 'AU807' plants were grown in 200 mm nursery pots which were filled with soilless potting media, maintained with granular slow release fertilizer, and regularly watered with overhead irrigation. No pest and disease measures were taken.

Those skilled in the art will appreciate that certain characteristics will vary with older or, conversely, younger plants. 'AU807' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 1986 edition. Note that generic color descriptions such as 'white' do not exist in The R.H.S. charts and the corresponding R.H.S. colors are quoted.

Technical Description of the Variety

Plant characteristics: 'AU807' is a short, tufted evergreen perennial. Average plant height is to 34 cm and average plant spread is 65 cm in a mature plant grown in a 200 mm nursery pot in Richmond, New South Wales, Australia. Propagation is accomplished by dividing the rhizomatous propagules which, collectively make up the crown of the plant. Said propagules will initiate new roots in approximately 2 to 3 weeks depending on the time of year and geographic location. An initial 4 to 7 months are needed to produce a well-rooted 200 mm pot, starting from a rooted cutting, depending on geographic location.

Leaf: Shape is linear; apex is emarginated, two-toothed, with each peak being acute; margin is entire; cross section is concave. Average length is 440 mm and the average width is 2 mm. Color of the adaxial and abaxial surfaces of the foliage is green corresponding to RHS 138A. Both the adaxial and abaxial surfaces are glaucous, however the abaxial surface displays a higher degree of glaucosity. With the glaucous wax removed, the color of the adaxial and abaxial surfaces is 143A. Both the adaxial and abaxial surfaces are glabrous in all stages of development. Venation pattern is parallel; vein color is indistinguishable from surrounding foliage. Basal sheath is membranous, long and acute, margins lacerate with a color that is closest to greyed purple 187A.

Roots: Many highly-branched, fibrous roots.

Inflorescence: Plants are dioceous with both male and female plants. Inflorescence are similar between the two with female inflorescence having slightly longer scapes and slightly larger flowers; otherwise the two sexes have similar inflorescences. Racemes ranging in length from 6 to 9 cm (average of 7 cm) containing small clusters of male flowers, or spikelets; some spikelets are sessile to the rachis while others are borne on pedicels of varying length. Peduncles range in length from 25 to 28 cm long and approximately 1.5 to 2 mm wide. Color of peduncle is greyed yellow 161C. Flowering period is heaviest in spring and sporadic at other times of the summer and fall. Inflorescence last for approximately 4 weeks.

Flowers: Male flowers only; flowers in spring or early summer. Very floriferous with approximately 70 matured inflorescences per 200 mm pot. Spikelets are either sessile to the rachis or borne on pedicels. Perianth consists of 4 elliptical petals that are approximately 4 mm in length with an approximate width across the perianth of 1.5 mm at the widest point. Apex is acute and slightly recurved. Perianth color is yellow 10B. Tepals number as three; color is greyed purple 187A. Six stamen of varying length are present. Pedicels range in length from 10 to 25 mm long and less than 1 mm wide; color is closest to yellow green 151A. Needle-shaped bracts present and range in length from 6 to 12 mm; apex is acute; margin is entire; color of bracts ranges from yellow 10D to greyed yellow 160D as they mature.

Reproductive organs: Female inflorescence are unbranched like the male, only with a slightly longer peduncle, otherwise similar to male inflorescence. Six reduced, sterile stamen; outer stamens inserted on rim of perianth tube; inner inserted on perianth, close to the outer, with filaments of varying length. Style short; stigma is capitate. Ovaries are superior.

Fruit and seed: Not observed.

Environmental Tolerances

Cold and heat tolerance: The winter hardiness of 'AU807' is at least to USDA Zone 8. 'AU807' has heat tolerance typical of *Lomandra fluviatilis*.

Drought tolerance: 'AU807' has excellent drought tolerance typical of *Lomandra fluviatilis* once established.

Pest resistance: No known insect pests. 'AU807' has disease tolerance typical of *Lomandra fluviatilis*.

Cultural conditions: 'AU807' is tolerant of a wide range of soil types and pH ranges.

Comparison of AU807 With Other Varieties of *Lomandra fluviatilis*

*Lomandra fluviatilis* is an under-commercialized species of *Lomandra* and, consequently, there has been little breeding work undertaken. For that reason, 'AU807' will be compared to the species, common-form *Lomandra fluviatilis* (unnamed), and the only commercialized selections known to the breeder, 'ABU7' (unpatented in the United States, Australian PBR Application no: 2008/308), which was an earlier selection from the same breeding program as 'AU807'. All three forms have similar foliage color, foliage texture, and bloom color. However the combination of improved vigor, a short plant height, an arching habit and a high number of inflorescences borne on long peduncles above the foliage makes 'AU807' distinguishable from the comparators.

'AU807' has a low plant height, reaching an average height of 34 cm whereas *Lomandra fluviatilis* 'ABU7' grows to approximately 40 cm high. While the overall plant height of 'AU807' is shorter than 'ABU7', the foliage of 'AU807' is longer which translates to a more compact and arching habit that is desirous to the ornamental plant industry. The foliage of 'AU807' is 44 cm long, on average, whereas the foliage of 'ABU7' is 37 cm on average. The foliage width of both is similar at 2 mm wide, giving both cultivars a comparable texture. Both cultivars have pronounced racemes borne on long peduncles. However, the racemes of 'AU807' are above the foliage whereas the racemes are at or slightly above the foliage; peduncles of 'AU807' are longer, measuring 26 cm on average compared to 20 cm in 'ABU7'. The racemes of both cultivars are similar in size (average of 7 cm for both) and in the number of spikelets (approximately 16 to 18). However, inflorescences are more numerous in 'AU807'.

'AU807' has a low plant height, reaching an average height of 34 cm whereas common-form *Lomandra fluviatilis* is much taller, reaching approximately 45 cm high. The foliage of 'AU807' is 44 cm long, on average, whereas the foliage of common-form *Lomandra fluviatilis* is 47 cm on average. These height and foliage dimensions translate to 'AU807' possessing an arching habit whereas common-form *Lomandra fluviatilis* has a semi-erect habit which is a distinguishable and significant difference to the ornamental plant industry. The foliage width of both cultivars is similar at 2 mm wide, giving both a comparable texture. The racemes of 'AU807' are above the foliage whereas the racemes of common-form *Lomandra fluviatilis* are below the foliage; peduncles of 'AU807' measure 26 cm on average compared to 28 cm in common-form *Lomandra fluviatilis*. At 10 cm long (on average) and approximately 18 to 22 spikelets per raceme, the raceme of common-form *Lomandra fluviatilis* is larger than that of 'AU807'. However, inflorescences are more numerous in 'AU807'.

The combination of improved vigor, a short plant height with long and arching foliage and a high number of inflorescences borne on long peduncles makes 'AU807' a desirable ornamental plant suited for mass production for pot and landscape use.

That which is claimed is:

1. A new and distinct variety of *Lomandra fluviatilis* plant named 'AU807', substantially as described and illustrated herein.

* * * * *